US00PP10209P

United States Patent [19]

Noodelijk

[11] Patent Number: Plant 10,209

[45] Date of Patent: Jan. 20, 1998

[54] CHRYSANTHEMUM PLANT NAMED 'CREAM REAGAN'

[76] Inventor: Robert Noodelijk, Vrouwgeestweg 26, 2481 KN Woubrugge, Netherlands

[21] Appl. No.: 738,606

[22] Filed: Oct. 29, 1996

[51] Int. Cl.[6] ..... A01H 5/00

[52] U.S. Cl. ..... Plt./82.2

[58] Field of Search ..... Plt./82.2, 74.1

*Primary Examiner*—Howard J. Locker

*Attorney, Agent, or Firm*—Parkhurst, Wendel & Burr, L.L.P.

[57] ABSTRACT

A new and distinct cultivar of Chrysanthemum plant named 'Cream Reagan', bearing small to medium sized pale yellow blooms with a yellow-green center and performance of 24–28 days.

2 Drawing Sheets

The cultivar 'Cream Reagan' as described and illustrated herein is related to the following cultivars:

'Dark Red Reagan' (U.S. Plant Pat. No. 9,929);
'Sunny Reagan' (U.S. Plant Pat. No. 9,928);
'Reagan' (U.S. Plant Pat. No. 8,642);
'Salmon Reagan' (U.S. Plant Pat. No. 8,869);
'Sulfur Reagan' (U.S. Plant Pat. No. 8,786);
'Dark Reagan' (U.S. Plant Pat. No. 8,966);
'Orange Reagan' (U.S. Plant Pat. No. 8,769);
'Bronze Reagan' (U.S. Plant Pat. No. 8,865);
'White Reagan' (U.S. Plant Pat. No. 8,784);
'Coral Reagan' (U.S. Plant Pat. No. 8,974);
'Yellow Reagan' (U.S. Plant Pat. No. 8,884);
'Dark Splendid Reagan' (U.S. Plant patent application Ser. No. 08/646,224); and
'Splendid Reagan' (U.S. Plant patent application Ser. No. 08/738,605).

BACKGROUND OF THE INVENTION

The present invention comprises a new and distinct cultivar of Chrysanthemum plant which is a natural occurring sport of a parent Chrysanthemum named 'Reagan'. Parent Chrysanthemum 'Reagan' is described in U.S. Plant Pat. No. 8,642. The new cultivar was discovered as a whole plant mutation in 1990 in a greenhouse in Holland.

The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a small to medium sized bloom and pale yellow color.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
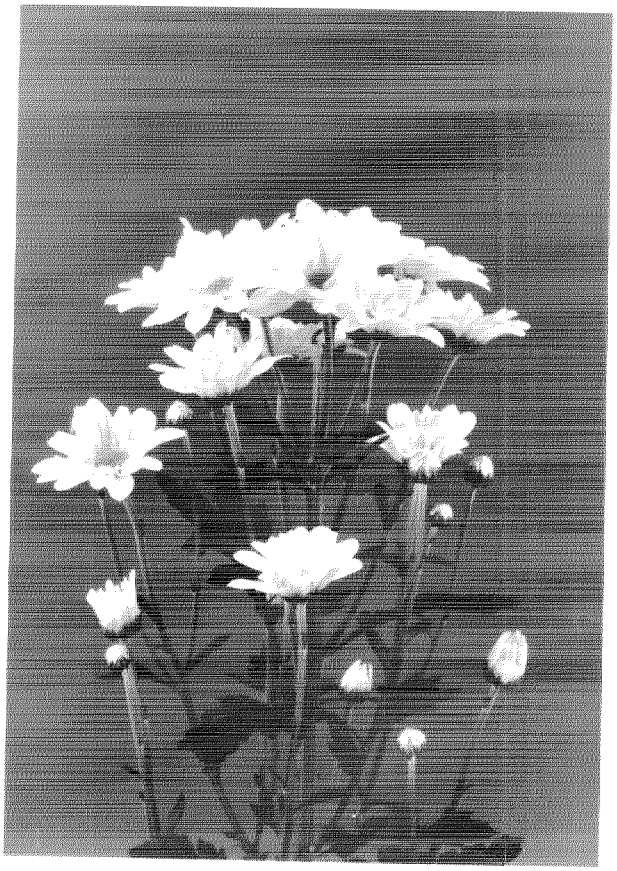
FIG. 1 shows the full bloom of the new cultivar.
Figure 2:
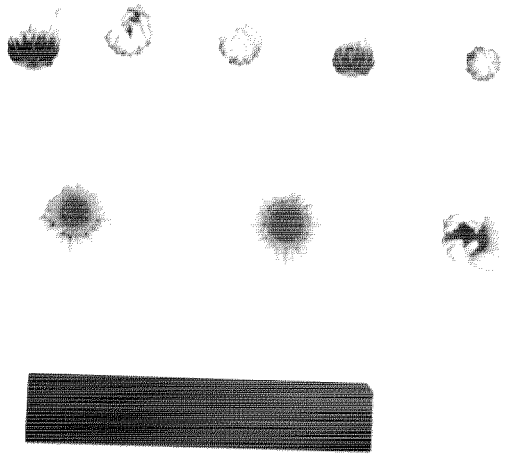
FIG. 2 shows the various stages of bloom of the new cultivar.
Figure 3:
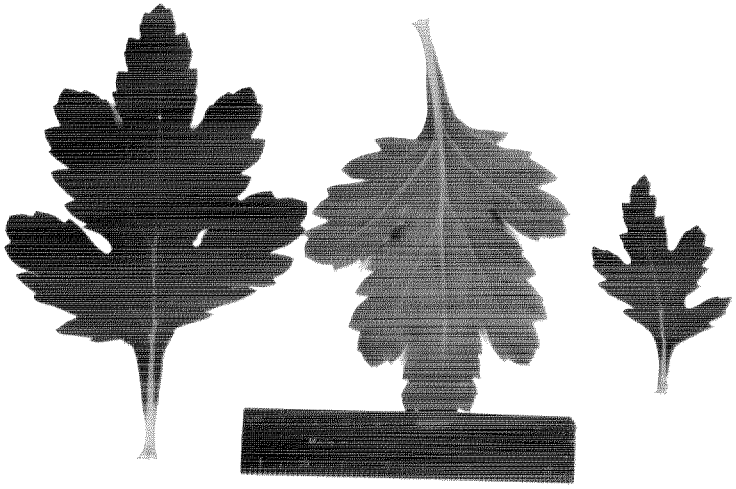
FIG. 3 shows foliage and petiole of the new cultivar.

This new variety of Chrysanthemum is of the botanical classification *Chrysanthemum morifolium*. When grown in the vicinity of Ter Aar, Holland, it has a response time of approximately 7½ weeks. This new variety produces small to medium sized pale yellow blooms with a yellow-green center having a 4 week performance (i.e., vase life of 24–28 days). This new variety of Chrysanthemum has been found to retain its distinctive characteristics throughout successive propagations and may be planted under greenhouse conditions in Holland between weeks 50 and 35.

The following is a description of the plant and characteristics (color designations are from R.H.S. Color Chart) that distinguish it from related known varieties and its antecedents. The color designations are taken from the plant itself. Accordingly, any discrepancies between the color designations and the colors depicted in the photographs are due to photographic tolerances.

Detailed Botanical Description and Comparative Data

| CULTIVAR | Cream Reagan | Sunny Reagan |
|---|---|---|
| Bud | | |
| Size | Medium cross section ±1.0 cm height ±0.7 cm | Medium cross section ±1.0 cm height ±0.7 cm |
| Form | Round and flat | Round and flat |
| Outside Color | Near Yellow 8A | Between Yellow 7A/Yellow 9A |
| Bloom | | |
| Size | Small to Medium | Medium |
| Fully Expanded | 6–6½ cm | 6½–7 cm |
| Borne | Upper portion single flower per peduncle lower portion plural flowers per peduncle | Upper portion, single flower per peduncle, lower portion plural flowers per peduncle |
| Peduncle Lengths | Near the top ±14 cm, near the middle ±24 cm near the bottom ±28 cm | Near the top ±14 cm, near the middle ±24 cm, near the bottom ±28 cm |
| Peduncle Lateral Shoot, Attachment | Medium | medium |
| Peduncle Lateral Shoot, Angle | Medium | medium |
| Form | Single (Daisy) | Single (Daisy) |
| Performance | Very good 24–28 days (18–20° C.) | Very good 24–28 days (18–20° C.) |

-continued

| Detailed Botanical Description and Comparative Data | | |
|---|---|---|
| Color Center of Flower: | | |
| Immature | Yellow-Green 143B | Yellow-Green 151C |
| Mature | Yellow-Green 154A | Yellow-Green 154A |
| Base of Petals | Nearest Yellow 4C | Yellow 5A deepening slightly to Yellow 6A in the basal half |
| Outer Petals | Nearest Yellow 4C | Yellow 5A deepening slightly to Yellow 6A in the basal half |
| Inside of Petals | Nearest Yellow 4C | Yellow 5A deepening slightly to Yellow 6A in the basal half |
| Reverse of Petals | Nearest Yellow 4C | Yellow 6A |
| Tonality from Distance | A pale yellow daisy with a fresh looking center having a little or no pollen | A yellow daisy with a fresh looking center having a little or no pollen |
| Discoloration | None | Some to Yellow 5B |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | Convex (no keels) | convex, two keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium to large (1.5–2.0 cm) | Medium to large (1.5–2.0 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Medium to tall | Strong |
| Height | 100–125 cm | 100–125 cm |
| Stem Color | Yellow-Green 143C | Yellow-Green 144A |
| Stem Strength | Medium | Strong |
| Stem Brittleness | Absent | Absent |
| Stem Anthocyanin Coloration | Absent | Present, mainly at the base |
| Internodes | 3–3½ cm | 3 cm |
| Flowering Response | 7½ weeks | 7½ weeks |

-continued

| Detailed Botanical Description and Comparative Data | | |
|---|---|---|
| Foliage | | |
| Color | Upperside green 137A. Underside Green 137C. | Upperside Green 137A. Underside Green 137C. |
| Size | Length ±12 cm. Width ±10 cm. | Length ±12 cm. Width ±9 cm. |
| Quantity | 22–28 | 22–28 |
| Shape | Lobed, see photograph | Lobed |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between Lateral Lobes | Converging | Converging |
| Shape of Base | Cordate | Truncate |
| Apex | Mucronate | Mucronate |
| Growth | | |
| Difference in average length | +5 cm | +10 cm |
| Response time | | |
| Difference in days of average response | +½ | +1½ |
| Response to ALAR | | |
| (g/100 l $H_2O$) | 300 | 450 |
| Year of Discovery | 1990 | 1991 |
| CULTIVAR | Yellow Reagan | Coral Reagan |
| Bud | | |
| Size | Medium cross section ±1.0 cm height ±0.7 cm | Medium cross section ±1.0 cm height ±0.7 cm |
| Form | Round and flat | Round and flat |
| Outside Color | Yellow 9C | Greyed Purple 186A |
| Bloom | | |
| Size | Medium | Medium |
| Fully Expanded | 6½–7 cm | 6½–7 cm |
| Borne | Upper portion single flower per peduncle, lower portion plural flowers per peduncle | Upper portion, single flower per peduncle, lower portion plural flowers per peduncle |
| Peduncle Lengths | Near the top ±14 cm, near the middle ±24 cm near the bottom ±28 cm | Near the top ±14 cm, near the middle ±24 cm, near the bottom ±28 cm |
| Peduncle Lateral Shoot, Attachment | weak to medium | weak to medium |
| Peduncle Lateral Shoot, Angle | small | small |
| Form | Single (Daisy) | Single (Daisy) |
| Performance | Very good 24–28 days (18–20° C.) | Very good 24–28 days (18–20° C.) |

-continued

| Detailed Botanical Description and Comparative Data | | |
|---|---|---|
| Color | | |
| Center of Flower: | | |
| Immature | Yellow-Green 151C | Yellow-Green 151C |
| Mature | Yellow-Green 154A | Yellow-Green 154A |
| Base of Petals | Yellow 5C | Greyed-Red 179C but redder |
| Outer Petals | Yellow 5C | Greyed Red 179C but redder |
| Inside of Petals | Yellow 5C | Greyed Red 179C but redder |
| Reverse of Petals | Yellow 4C | Greyed Yellow 162D tinged with Red Purple 71B between ribs and margin |
| Tonality from Distance | A yellow daisy with a fresh looking center having a little or no pollen | A pale bronze daisy with a fresh looking center having a little or no pollen |
| Discoloration | Some to yellow 5B | Some to yellow-orange 23C |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | flat, two keels | flat, two keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium (1.5 cm) | Medium (1.5 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Strong | Strong |
| Height | 100–125 cm | 100–125 cm |
| Stem Color | Yellow-Green 146B | Yellow-Green 144A |
| Stem Strength | Medium | Medium |
| Stem Brittleness | Absent | Absent |
| Stem Anthocyanin Coloration | Absent | Present |
| Internodes | 3 cm | 3 cm |
| Flowering Response | 7½ weeks | 7½ weeks |
| Foliage | | |
| Color | Upperside green 137A. Underside Green 137C. | Upperside Green 137A. Underside Green 137C. |

-continued

| Detailed Botanical Description and Comparative Data | | |
|---|---|---|
| Size | Length ±12 cm. Width ±9 cm. | Length ±12 cm. Width ±9 cm. |
| Quantity | 22–28 | 22–28 |
| Shape | Lobed | Lobed |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between Lateral Lobes | Parallel | Converging |
| Shape of Base | Asymmetric | Asymmetric |
| Apex | Mucronate | Cuspidate |
| Growth | | |
| Difference in average length | 0 | −5 cm |
| Response time | | |
| Difference in days of average response | +1 | +1 |
| Response to ALAR | | |
| (g/100 l $H_2O$) | 280 | 250 |
| Year of Discovery | 1990 | 1998 |
| CULTIVAR | Bronze Reagan | Salmon Reagan |
| Bud | | |
| Size | Medium cross section ±1.0 cm height ±0.7 cm | Medium cross section ±1.0 cm height ±0.7 cm |
| Form | Round and flat | Round and flat |
| Outside Color | Greyed Red 179C | Nearest to Yellow 23D |
| Bloom | | |
| Size | Medium | Medium |
| Fully Expanded | 6½–7 cm | 6½–7 cm |
| Borne | Upper portion, single flower per peduncle, lower portion plural flowers per peduncle | Upper portion, single flower per peduncle, lower portion plural flowers per peduncle |
| Peduncle Lengths | Near the top ±14 cm, near the middle ±24 cm near the bottom ±28 cm | Near the top ±14 cm, near the middle ±24 cm, near the bottom ±28 cm |
| Peduncle Lateral Shoot, Attachment | weak | medium |
| Peduncle Lateral Shoot, Angle | small | medium |
| Form | Single (Daisy) | Single (Daisy) |
| Performance | Very good 24–28 days (18–20° C.) | Very good 24–28 days (18–20° C.) |
| Color | | |
| Center of Flower: | | |
| Immature | Yellow-Green 151C | Yellow-Green 151C |
| Mature | Yellow-Green 154A | Yellow-Green 154A |

-continued

| Detailed Botanical Description and Comparative Data | | |
|---|---|---|
| Base of Petals | Yellow 8A with an overlay of Greyed Red | Nearest to orange 29C 179B |
| Outer Petals | Yellow 8A with an overlay of Greyed Red 179B | Nearest to orange 29C |
| Inside of Petals | Yellow 8A an overlay of Greyed Red 179B | Nearest to orange 29C |
| Reverse of Petals | Yellow 8C tinged along the center with Greyed Red 179B in a tesselated pattern | Nearest to orange 22D |
| Tonality from Distance | A pale bronze daisy with a fresh looking center having a little or no pollen | A yellow-orange to orange daisy with a fresh looking center having a little or no pollen |
| Discoloration | None | None |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | flat, two keels | flat, two keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium (1.5 cm) | Medium (1.5 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Strong | Strong |
| Height | 100–125 cm | 100–125 cm |
| Stem Color | Yellow-Green 144A | Yellow-Green 144A |
| Stem Strength | Medium | Medium |
| Stem Brittleness | Absent | Present |
| Stem Anthocyanin Coloration | Present | Present |
| Internodes | 3 cm | 3 cm |
| Flowering Response | 7½ weeks | 7½ weeks |
| Foliage | | |
| Color | Upperside green 137A. Underside Green 137C. | Upperside Green 137A. Underside Green 137C. |
| Size | Length ±12 cm. Width ±9 cm. | Length ±12 cm. Width ±9 cm. |

-continued

| Detailed Botanical Description and Comparative Data | | |
|---|---|---|
| Quantity | 22–28 | 22–28 |
| Shape | Lobed | Lobed |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between Lateral Lobes | Converging | Parallel |
| Shape of Base | Asymmetric | Asymmetric |
| Apex | Cuspidate | Cuspidate |
| Growth | | |
| Difference in average length | 0 | +10 cm |
| Response time | | |
| Difference in days of average response | −½ | 0 |
| Response to ALAR | | |
| (g/100 l $H_2O$) | 250 | 450 |
| Year of Discovery | 1998 | 1997 |
| CULTIVAR | Sulfur Reagan | Parent Cultivar Reagan |
| Bud | | |
| Size | Medium cross section ±1.0 cm height ±0.7 cm | Medium cross section ±1.0 cm height ±0.7 cm |
| Form | Round and flat | Round and flat |
| Outside Color | Yellow 10C | Greyed Purple 186D but paler |
| Bloom | | |
| Size | Medium | Medium |
| Fully Expanded | 7–7½ cm | 6½–7 cm |
| Borne | Upper portion single flower per peduncle, lower portion plural flowers per peduncle | Upper portion, single flower per peduncle, lower portion plural flowers per peduncle |
| Peduncle Lengths | Near the top ±14 cm, near the middle ±24 cm near the bottom ±28 cm | Near the top ±14 cm, near the middle ±24 cm, near the bottom ±28 cm |
| Peduncle Lateral Shoot, Attachment | weak to medium | Medium |
| Peduncle Lateral Shoot, Angle | small | Medium |
| Form | Single (Daisy) | Single (Daisy) |
| Performance | Very good 24–28 days (18–20° C.) | Very good 24–28 days (18–20° C.) |
| Color | | |
| Center of Flower: | | |
| Immature | Yellow-Green 151C | Yellow-Green 151C |
| Mature | Yellow-Green 154A | Yellow-Green 154A |
| Base of Petals | Yellow 6D | Purple 75B |
| Outer Petals | Yellow 6D | Purple 75B |
| Inside of Petals | Yellow 6D | Purple 75B |
| Reverse of Petals | Yellow 6D | Red-Purple 69D but paler |

-continued

| Detailed Botanical Description and Comparative Data | | |
|---|---|---|
| Tonality from Distance | A yellow daisy with a fresh looking center having a little or no pollen | A pale pink daisy with a fresh looking center having a little or no pollen |
| Discoloration | None | Some to Red-Purple 69D |
| Pollen | Yellow-Orange 14A | Yellow-Orange 14A |
| Petals | | |
| Texture | Upperside smooth, underside smooth | Upperside smooth, underside smmoth |
| Number | 24–30 (two rows) | 24–30 (two rows) |
| Cross-section | flat, two keels | flat, two keels |
| Arrangement | Imbricated | Imbricated |
| Persistence | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium (1.5 cm) | Medium (1.5 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Strong | Strong |
| Height | 100–125 cm | 100–125 cm |
| Stem Color | nearest Green 143C | Yellow-Green 144A |
| Stem Strength | Medium to strong | Medium |
| Stem Brittleness | Absent | Present |
| Stem Anthocyanin Coloration | Absent | Absent |

-continued

| Detailed Botanical Description and Comparative Data | | |
|---|---|---|
| Internodes | 3 cm | 3 cm |
| Flowering Response | 7½ weeks | 7½ weeks |
| Foliage | | |
| Color | Upperside Green 137A. Underside Green 137C. | Upperside Green 137A. Underside Green 137C. |
| Size | Length ±12 cm. Width ±9 cm. | Length ±12 cm. Width ±9 cm. |
| Quantity | 22–28 | 22–28 |
| Shape | Lobed | Lobed |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between Lateral Lobes | Parallel | Converging |
| Shape of Base | Asymmetric | Rounded |
| Apex | Mucronate | Cuspidate |
| Growth | | |
| Difference in average length | +10 cm | 0 |
| Response time | | |
| Difference in days of average response | −1 | 0 |
| Response to ALAR | | |
| (g/100 l $H_2O$) | 450 | 300 |
| Year of Discovery | 1990 | 1996 |

I claim:

1. A new and distinct variety of Chrysanthemum plant as described and illustrated.

* * * * *